(12) United States Patent
Chan

(10) Patent No.: US 9,943,222 B2
(45) Date of Patent: Apr. 17, 2018

(54) LARYNGOSCOPE WITH AUTOMATIC IMAGE ADJUSTMENT

(71) Applicants: IEI INTEGRATION CORP., New Taipei (TW); ARMORLINK SH CORP., Shanghai (CN)

(72) Inventor: Kai-Cheng Chan, New Taipei (TW)

(73) Assignees: IEI Integration Corp., New Taipei (TW); Armorlink SH Corp., Shanghai (CN)

( * ) Notice: Subject to any disclaimer, the term of this patent is extended or adjusted under 35 U.S.C. 154(b) by 726 days.

(21) Appl. No.: 14/557,768

(22) Filed: Dec. 2, 2014

(65) Prior Publication Data

US 2016/0022132 A1 Jan. 28, 2016

(30) Foreign Application Priority Data

Jul. 22, 2014 (CN) ...................... 2014 2 0406912 U

(51) Int. Cl.
*A61B 1/00* (2006.01)
*A61B 1/267* (2006.01)
*A61B 1/04* (2006.01)
*A61B 1/06* (2006.01)

(52) U.S. Cl.
CPC .......... *A61B 1/267* (2013.01); *A61B 1/00006* (2013.01); *A61B 1/00048* (2013.01); *A61B 1/00052* (2013.01); *A61B 1/00128* (2013.01); *A61B 1/04* (2013.01); *A61B 1/06* (2013.01)

(58) Field of Classification Search
USPC ................ 396/381, 383; 348/333.01–333.13
See application file for complete search history.

(56) References Cited

U.S. PATENT DOCUMENTS

| | | | | |
|---|---|---|---|---|
| 5,659,361 A | * | 8/1997 | Jin ....................... | H04N 5/2251 248/921 |
| 5,827,178 A | * | 10/1998 | Berall ................... | A61B 1/267 600/185 |
| 6,115,069 A | * | 9/2000 | Kuroki ................. | H04N 5/2251 348/373 |
| 6,226,448 B1 | * | 5/2001 | Takagi .................. | H01R 35/02 348/207.99 |
| 6,573,939 B1 | * | 6/2003 | Yokoyama ........... | H04N 5/2251 348/333.06 |
| 6,741,287 B1 | * | 5/2004 | Fuchimukai ......... | H04N 5/2251 348/333.06 |

(Continued)

*Primary Examiner* — David Bates
(74) *Attorney, Agent, or Firm* — Rosenberg, Klein & Lee

(57) ABSTRACT

A laryngoscope with automatic image adjustment is revealed. The laryngoscope includes a laryngoscope body, a rotation assembly, a display and a sensor. The laryngoscope body is disposed with a fixing slot and is used for capturing an image. One end of the rotation assembly is fixed in the fixing slot while the other end thereof is arranged with the display. The display is rotated around the rotation assembly. The rotation assembly is set with a limiting slot. The sensor is electrically connected to a rear side of the display and is located inside the limiting slot. While the display being rotated, the sensor is slid on the surface of the rotation assembly. When the sensor is slid in the limiting slot, the display shows the image. Once the sensor is slid outside the limiting slot, the display shows a reflection of the image. Thus the image is adjusted automatically.

10 Claims, 28 Drawing Sheets

(56) References Cited

U.S. PATENT DOCUMENTS

| | | | |
|---|---|---|---|
| 7,046,286 B1* | 5/2006 | Kobayashi | H04N 5/23216 348/333.06 |
| 7,145,593 B2* | 12/2006 | Yamaguchi | G06F 1/1616 348/14.02 |
| 7,190,968 B2* | 3/2007 | Nakamura | H04M 1/0214 345/169 |
| 7,215,355 B2* | 5/2007 | Kim | H04N 5/2253 348/14.01 |
| 7,295,240 B2* | 11/2007 | Kobayashi | H04N 5/2251 348/14.01 |
| 7,331,724 B2* | 2/2008 | Hasegawa | H04M 1/0229 345/169 |
| 7,349,021 B2* | 3/2008 | Okada | G06F 1/1616 348/333.06 |
| 7,626,630 B2* | 12/2009 | Nishino | H04M 1/0216 348/333.06 |
| 8,159,593 B2* | 4/2012 | Takahashi | H04N 5/23293 348/333.06 |
| 8,715,172 B1* | 5/2014 | Girgis | A61B 1/267 600/188 |
| 9,013,619 B2* | 4/2015 | Kim | H04N 5/2251 348/333.06 |
| 2001/0004269 A1* | 6/2001 | Shibata | H04M 1/021 348/333.06 |
| 2002/0022769 A1* | 2/2002 | Smith | A61B 1/00052 600/188 |
| 2004/0116167 A1* | 6/2004 | Okuzako | H04M 1/0214 455/575.3 |
| 2004/0174452 A1* | 9/2004 | Kinemura | H04N 5/2252 348/333.06 |
| 2005/0280732 A1* | 12/2005 | Misawa | H04N 5/2251 348/333.06 |
| 2007/0298850 A1* | 12/2007 | Miyata | H04M 1/021 455/575.3 |
| 2008/0106606 A1* | 5/2008 | Ho | H04N 5/23293 348/333.06 |
| 2010/0249513 A1* | 9/2010 | Tydlaska | A61B 1/00052 600/186 |
| 2013/0018227 A1* | 1/2013 | Schoonbaert | A61B 1/00052 600/188 |
| 2015/0112146 A1* | 4/2015 | Donaldson | A61B 1/00048 600/188 |

* cited by examiner

LARYNGOSCOPE WITH AUTOMATIC IMAGE ADJUSTMENT

BACKGROUND OF THE INVENTION

Fields of the Invention

The present invention relates to a laryngoscope, especially to a laryngoscope with automatic image adjustment for different conditions.

Descriptions of Related Art

For critically injured or anesthetized patients, medical staff needs to place a flexible plastic tube into the trachea of the patient for providing oxygen and facilitating ventilation while the patient is in emergency situations or is unconscious due to general anesthesia.

The laryngoscope can be inserted into most of the patient's mouth by doctors with certain experience for placement of the tracheal tube. Yet about 20% patients have a short lower jaw, a hard neck or a short neck that may lead to difficulties in seeing the tracheal opening. Thus a camera lens is arranged at the front end of the laryngoscope and is connected to a large screen by wires for monitoring images captured by the laryngoscope. However, the large screen is having poor portability. For beginners, the use of laryngoscope to intubate the trachea and monitor the large screen simultaneously is difficult. Thus a new design of an integrated laryngoscope has been developed. A camera lens is disposed on the front end of a blade of the integrated laryngoscope and a light source is beside the camera lens. A smaller screen is arranged at an upper side of the handle. Thus the integrated laryngoscope is easy to use. The viewing angle of the screen is restricted by field of view of the camera lens. If the viewing angle is too low or too high, images on the screen are unable to be viewed clearly. This causes inconvenience in the use of the laryngoscope.

Moreover, patients in a comatose state caused by drowning, blows or other factors need to be maintained an open airway and ensure adequate ventilation. If the patient is vomiting, or the airway may be obstructed by foreign bodies, the rescuer must open the patient's mouse first and observe the patient's larynx carefully to confirm whether the airway is obstructed. If the airway is blocked, certain measures are applied as soon as possible to remove foreign bodies for preventing airway obstruction and poor ventilation.

Generally the patient's tongue base may fall back or collapse to obstruct the larynx when the rescuer opens the mouth of unconscious patient to observe patient's larynx. This causes difficulties in observation of the airway. Once the rescuer has poor vision, the deeper site of the larynx is difficult to be observed. Moreover, there are certain blind spots while observing the larynx. The rescuer with insufficient expertise and experience is unable to see these places.

Thus a device for laryngeal observation is provided. The device consists of a handle and a blade. The handle is grasped by a user and is mounted with a power supply unit therein. One end of the blade is pressed on a tongue base so as to prevent the tongue base from occluding the larynx. Moreover, the blade is arranged with a light and a camera, both connected to the power supply unit by wires. The light is used for lighting the patient's larynx and the camera is used to capture images of the patient's larynx. By a transmission line, the images captured are transmitted to a display. Thus the users can observe the patient's larynx and this is more convenient for the rescuing work.

Although the above device allows the user to observe the patient's larynx more conveniently, the wires for power supply and the transmission line for sending images not only increase total weight and complexity of the device but also affect portability of the display. The display is unable to be moved conveniently according to the rescuer's requirements. The image shown on the display is also unable to be adjusted automatically during rotation of the display according to the patient's position. This also leads to inconvenience in use.

SUMMARY OF THE INVENTION

Therefore it is a primary object of the present invention to provide a laryngoscope with automatic image adjustment in which whether an image captured now is reflected or not is determined by a position of a sensor inside or outside of a limiting slot. Thus the automatic image adjustment is achieved and the convenience in use is improved.

In order to achieve the above object, a laryngoscope with automatic image adjustment of the present invention includes a laryngoscope body, a rotation assembly, a display and a sensor. The laryngoscope body is mounted with a fixing slot while the rotation assembly is arranged with a limiting slot. One end of the rotation assembly is connected to the fixing slot while the other end thereof is connected to the display. The sensor is at a rear side of the display. When the display is rotated and the sensor is in the limiting slot, the display shows an image. Once the display is rotated to make the sensor become outside the limiting slot, the display shows a reflection of the image. By the sensor detecting that the display has been rotated to a preset angle, the display is driven to show a reflection of the image.

Thus the image is adjusted automatically and the laryngoscope is more convenient to use.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
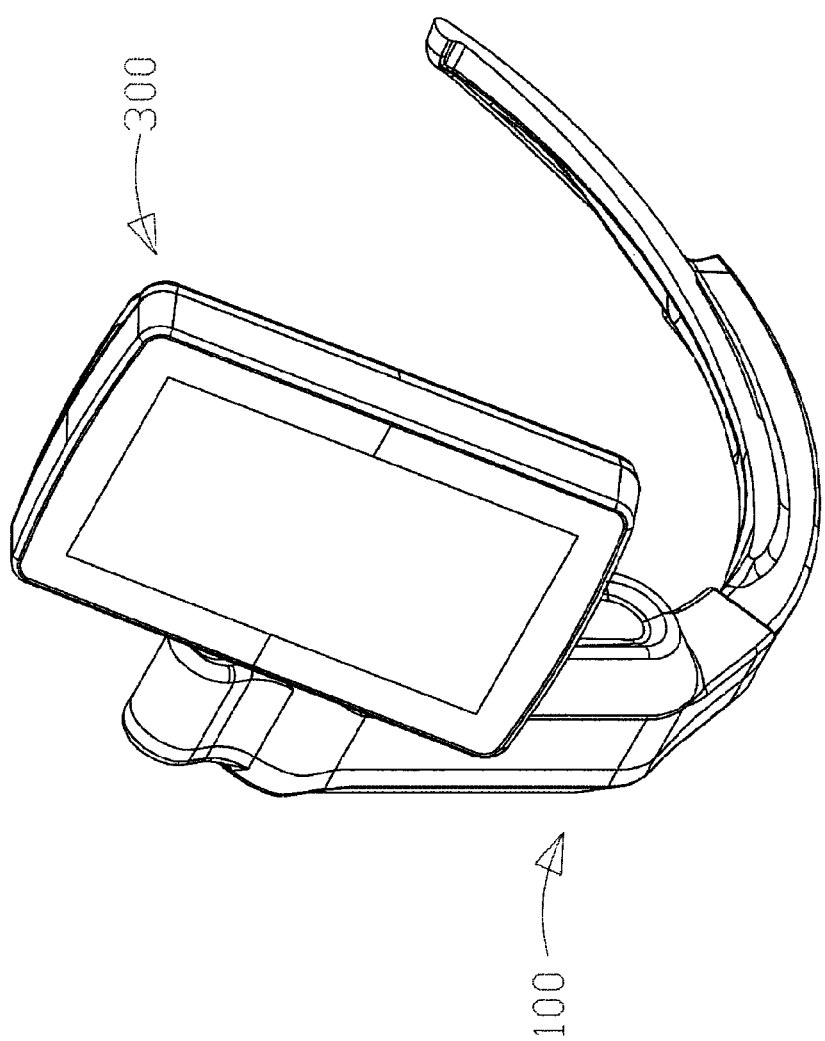
FIG. 1 is a perspective view of an embodiment according to the present invention.
Figure 2:
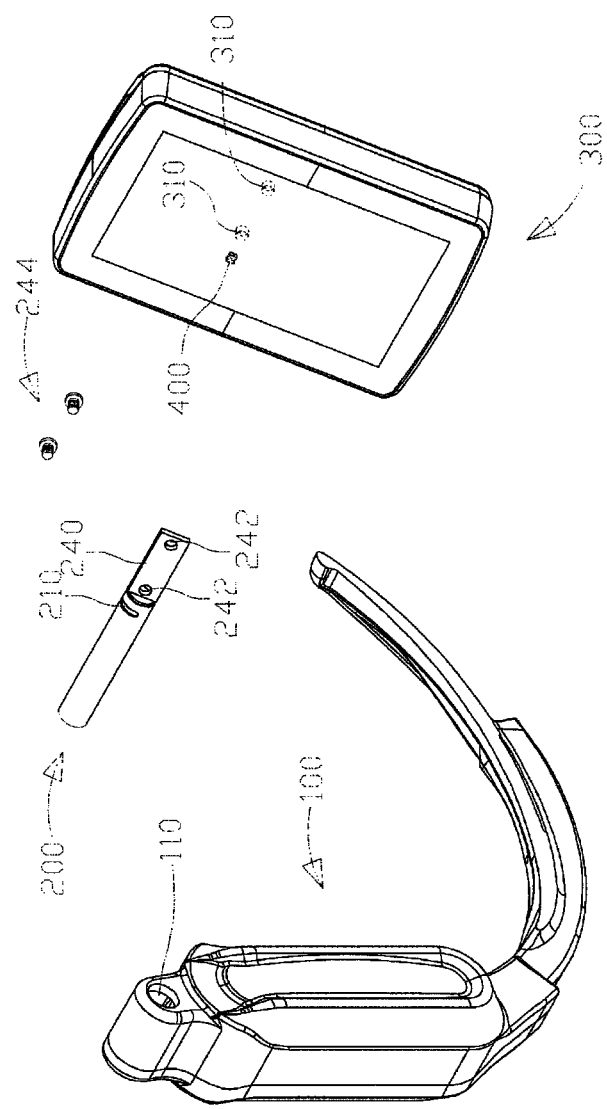
FIG. 2 is an explosive view of an embodiment according to the present invention.

Refer to FIG. 1 and FIG. 2, a laryngoscope with automatic image adjustment of the present invention includes a laryngoscope body 100, a rotation assembly 200, a display 300 and a sensor 400. The laryngoscope body 100 is disposed with a fixing slot 110, the laryngoscope body 100 is used for capturing an image. One end of the rotation assembly 200 is mounted and fixed in the fixing slot 110 while the other end of the rotation assembly 200 is arranged with the display 300. Thus the display 300 is rotated around the rotation assembly 200. The rotation assembly 200 is set with a limiting slot 210. The display 300 is used to show the image. The sensor 400 is electrically connected to a rear side of the display 300. The sensor 400 is located inside the limiting slot 210. While the display 300 being rotated, the sensor 400 is slid on the surface of the rotation assembly 200. If the sensor 400 is slid in the limiting slot 210, the display 300 shows the image. Once the sensor 400 is slid out of the limiting slot 210, the display 300 shows a reflection of the image. For example, the display 300 shows a first image when the sensor 400 is slid in the limiting slot 210. While the sensor 400 being slid out of the limiting slot 210, the display 300 shows a second image. Compared to the first image, the second image is a reflection of the first image with upside down.

Thus the present invention checks the angle of the display 300 by the sensor 400. According to the position of the sensor 400 relative to the limiting slot 210, the image on the display 300 is switched between the image captured and the reflection of the image captured. When the user rotates the display 300 over a certain angle, the image is adjusted automatically. The laryngoscope of the present invention is more convenient to use. The display 300 is not only able to be rotated relative to the position of the rescuer, but also able to automatically adjust the image displayed according to the position of the rescuer. For example, while people are unconscious in outdoors due to drowning, hits or other factors and unsuitable to be moved, the image showed on the display 300 can be adjusted automatically according to the angle of the display 300 being rotated by the rescuer. The device is more convenient to use.

Figure 3:
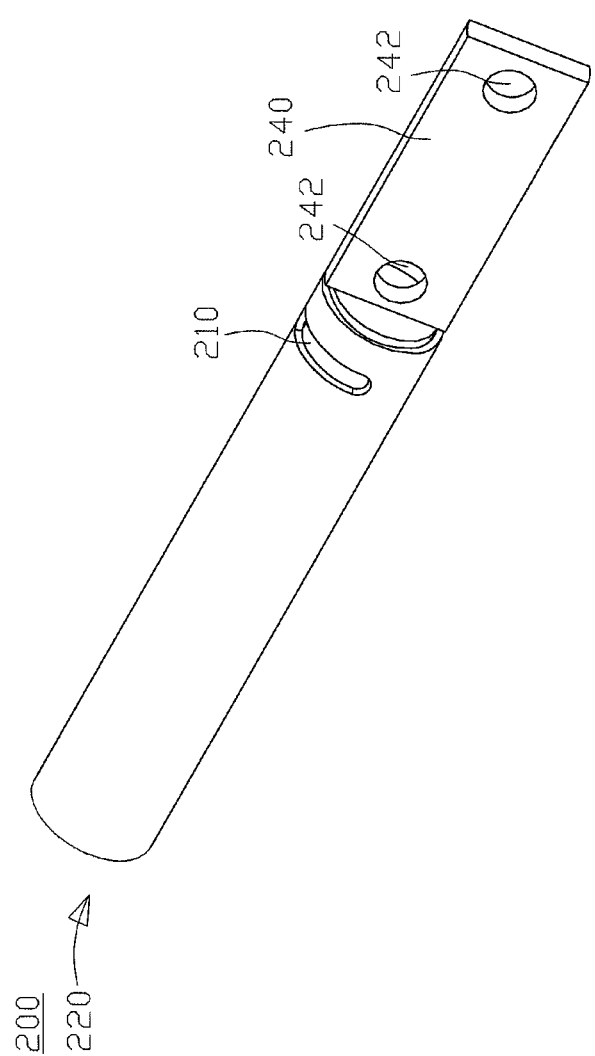
FIG. 3 is a perspective view of a rotation assembly of an embodiment according to the present invention.
Figure 4:
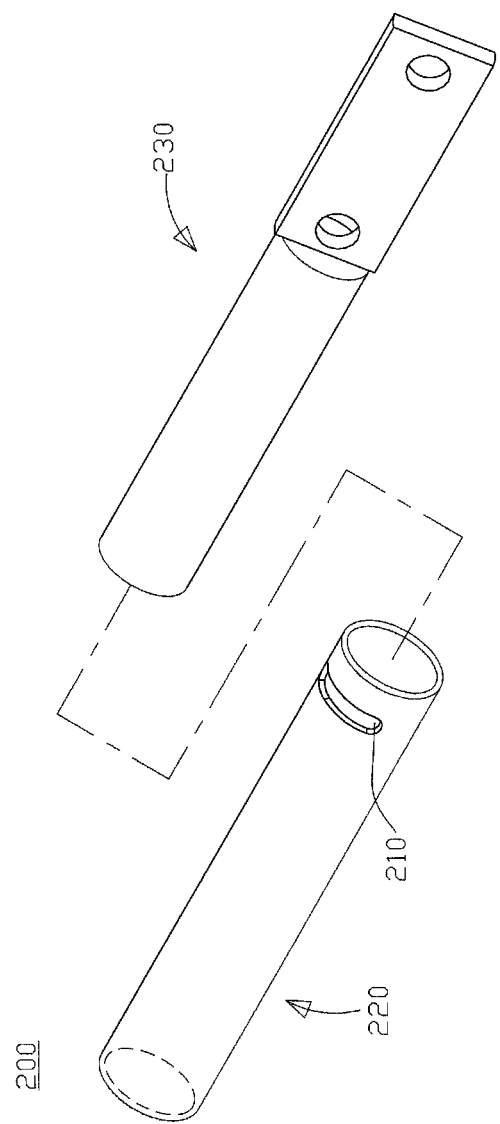
FIG. 4 is an explosive view of a rotation assembly of an embodiment according to the present invention.

Refer to FIG. 3 and FIG. 4, the rotation assembly 200 of the present invention consists of a hollow tube 220 and a rotating shaft 230. The hollow tube 220 is mounted in the fixing slot 110 (as shown in FIG. 2) while the rotating shaft 230 is pivotally arranged in the hollow tube 220. Thus the rotating shaft 230 is rotated in the hollow tube 220. The display 300 is fixed on the rotating shaft 230 (as shown in FIG. 2). Thus the display 300 is rotated around the rotating shaft 230. The limiting slot 210 is arranged at a sidewall of the hollow tube 220 and the limiting slot 210 is penetrating the sidewall of the hollow tube 220. Thus the rotating shaft 230 is in contact with the sidewall of the hollow tube 220 through the limiting slot 210 while the rotating shaft 230 being pivotally disposed in the hollow tube 220. In this embodiment, the sensor 400 is a push button switch or a pressure sensor. When the display 300 is rotated by the rotating shaft 230, the sensor 400 is slid on the surface of the hollow tube 220 around the rotating shaft 230. The image displayed is switched between the image captured and the reflection of the image due to the sensor 400 slid into and out of the limiting slot 210. Thus the convenience in use of the present invention is improved.

Figure 5:
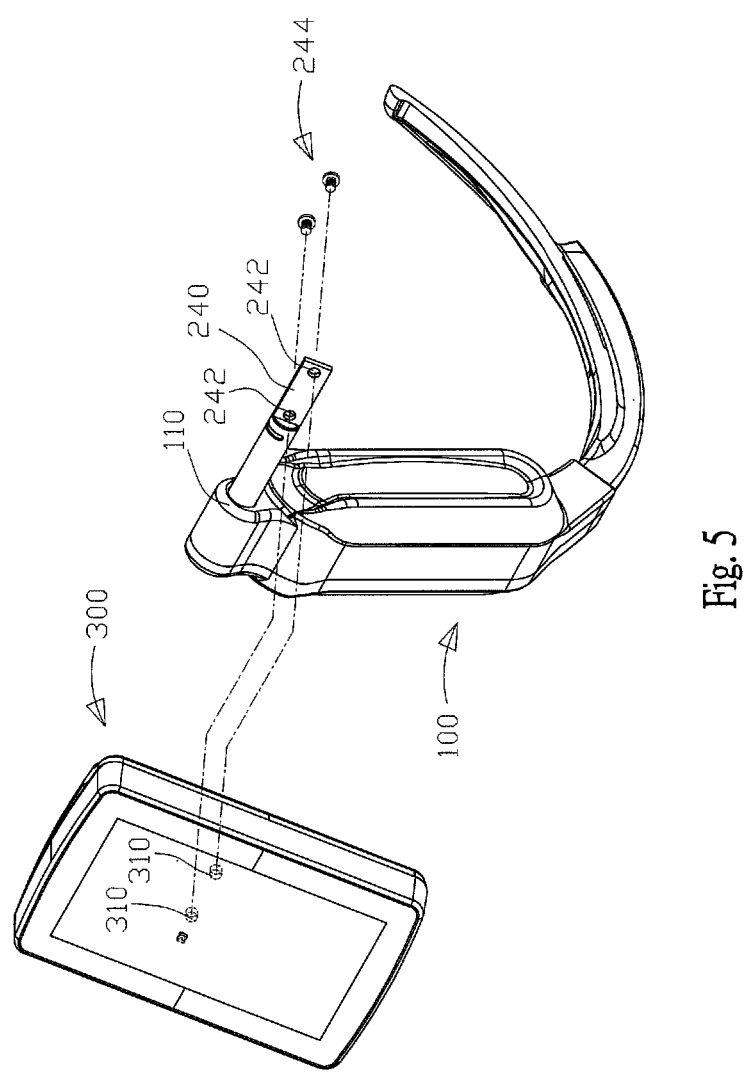
FIG. 5 is a schematic drawing showing a first step during assembly of an embodiment according to the present invention.

Refer to FIG. 5, a schematic drawing showing assembling of an embodiment of a laryngoscope according to the present invention is revealed. The rotating shaft 230 is further disposed with a fixing portion 240 that is used for fixing the display 300 on the rotating shaft 230. A plurality of spacing holes 242 is disposed on the fixing portion 240 while a plurality of fixing holes 310 is arranged at the rear side of the housing of the display 300. The positions of the spacing holes 242 are corresponding to the positions of the fixing holes 310. A plurality of fasteners 244 is inserted through the spacing holes 242 and then is fastened and fixed in the fixing holes 310. Thus the display 300 is firmly disposed on the rotating shaft 230.

Figure 6:
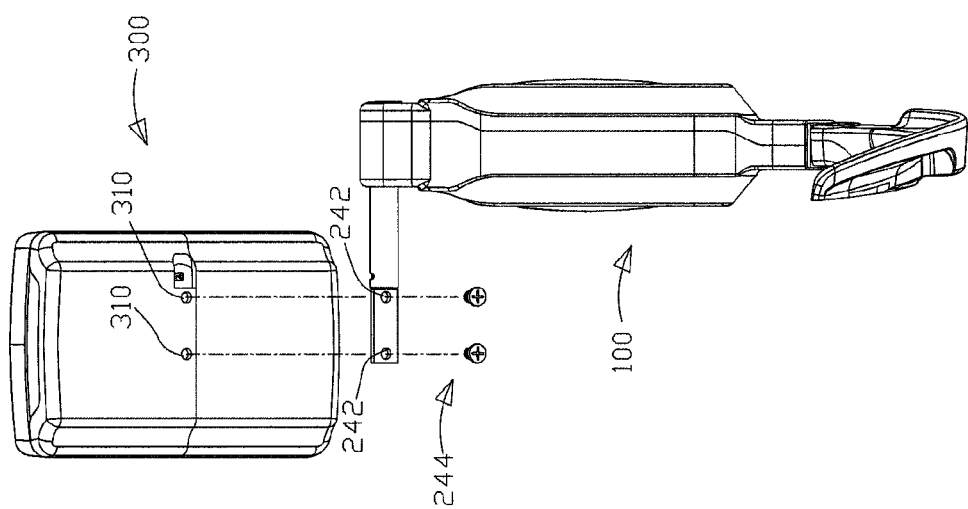
FIG. 6 is a schematic drawing showing a second step during assembly of an embodiment according to the present invention.
Figure 7:
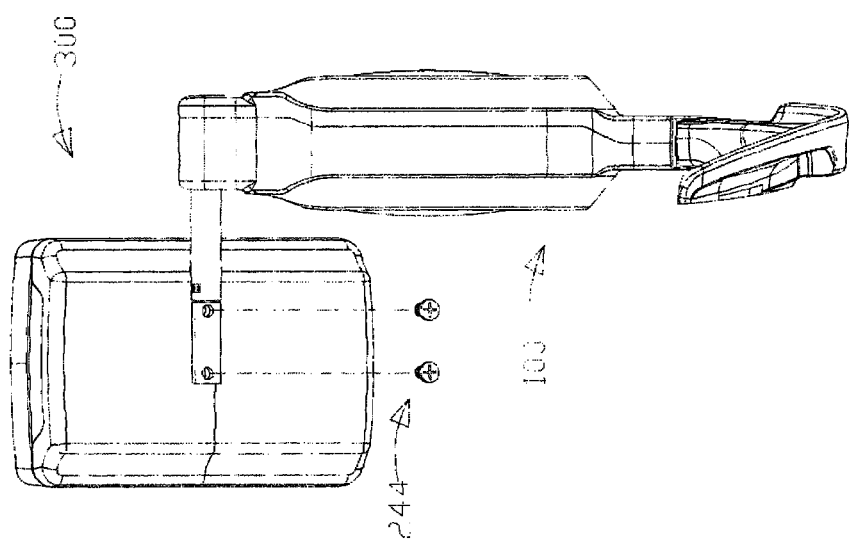
FIG. 7 is a schematic drawing showing a third step during assembly of an embodiment according to the present invention.

Refer to FIG. 5, FIG. 6 and FIG. 7, how the laryngoscope of the present invention is assembled is revealed. As shown in FIG. 5, first the hollow tube 220 of the rotation assembly 200 is fixed inside the fixing slot 110. Then the spacing holes 242 of the fixing portion 240 are aligned with the fixing holes 310 on the rear side of the display 300, as shown in FIG. 6. Next refer to FIG. 7, fasteners 244 such as screws are inserted through the spacing holes 242 to be fixed in the fixing holes 310. Thus the display 300 is fixed on the rotating shaft 230 and the display 300 is able to rotate around the rotating shaft 230 clockwise or counterclockwise.

Figure 8:
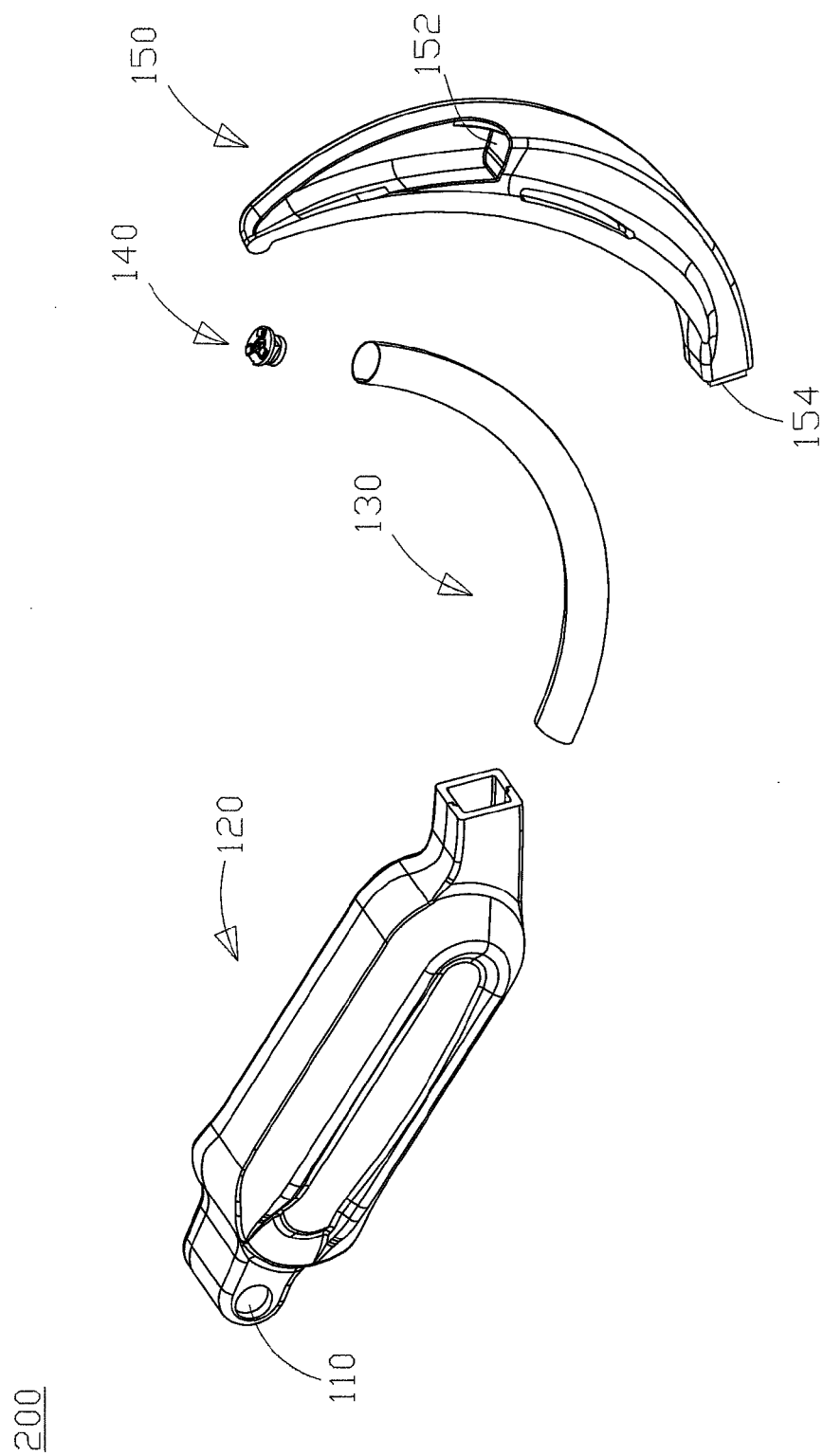
FIG. 8 is an explosive view of a laryngoscope body of an embodiment according to the present invention.

Refer to FIG. 8, an explosive view of an embodiment of the laryngoscope body 100 according to the present invention is revealed. The laryngoscope body 100 consists of a handle 120, a tube 130, a camera lens 140 and a blade 150. A first end of the handle 120 is set with the fixing slot 110 while a second end of the handle 120 is disposed with the tube 130. In this embodiment, the fixing slot 110 is set on an upper side of the handle 120 while a lower side of the handle 120 is arranged with an opening. The tube 130 is arranged at the lower side of the handle 120 through the opening. The camera lens 140 is mounted into the front end of the tube 130 and the camera lens 140 is used for capturing images and transmitting the images to the display 300 to be displayed. The blade 150 is disposed around the tube 130 and the blade 150 connected to the second end of the handle 120. The blade 150 is having a transparent window 152 for allowing the camera lens 140 to take images.

Figure 9:
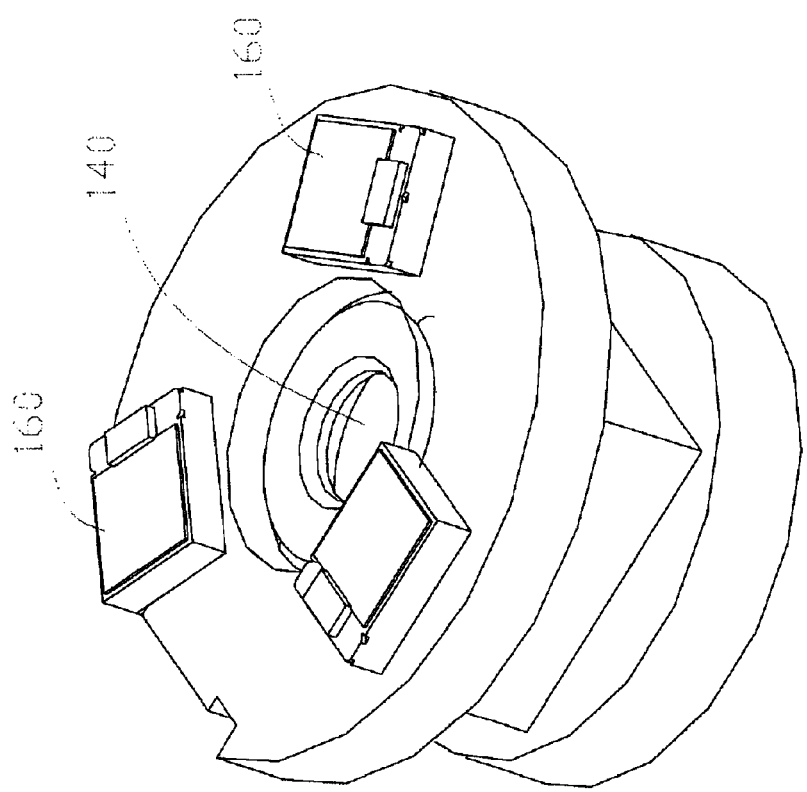
FIG. 9 is a perspective view of a camera lens of an embodiment according to the present invention.

Moreover, as shown in FIG. 9, the laryngoscope body 100 further includes at least one lighting unit 160 arranged at the camera lens 140. The lighting unit 16 provides light to the camera lens 140. Thus the images captured by the camera lens 140 are getting clear. Therefore the rescuer can get access and treat the patient more quickly.

Still refer to FIG. 8, the handle 120, the tube 130, the camera lens 140 and the blade 150 are arranged from the left side to the right side in turn for assembly of the laryngoscope body 100. Then the tube 130 is pivotally connected to the second end of the handle 120. Next the camera lens 140 is mounted in the tube 130 and the camera lens 140 located at the front end of the tube 130. At last, the blade 150 is disposed around the tube 130 and a connection portion 154 of the blade 150 is connected to the second end of the handle 120. The assembly of the laryngoscope body 100 is completed.

Figure 10:
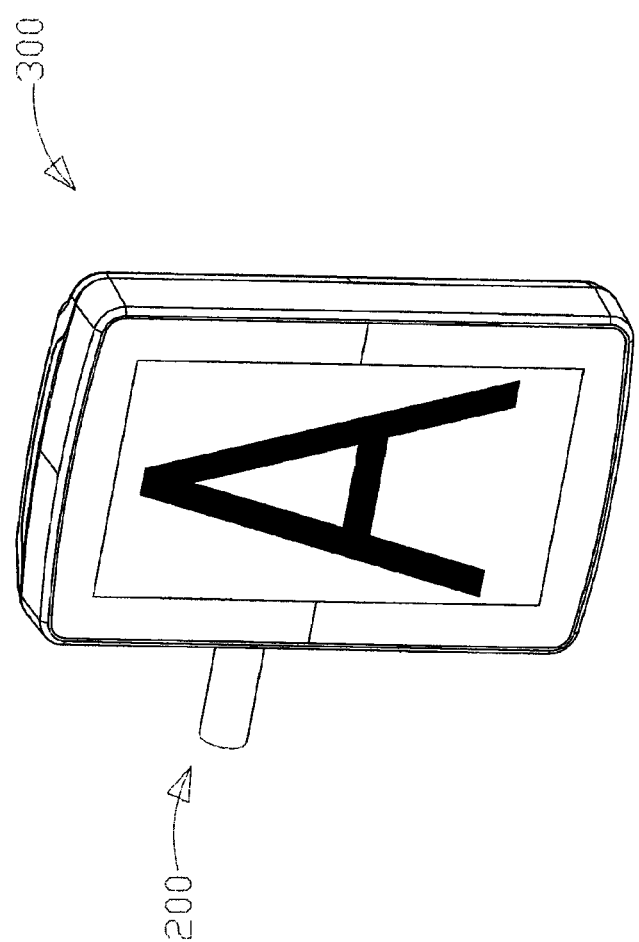
FIG. 10 is a schematic drawing showing an image on a display of an embodiment according to the present invention.
Figure 11:
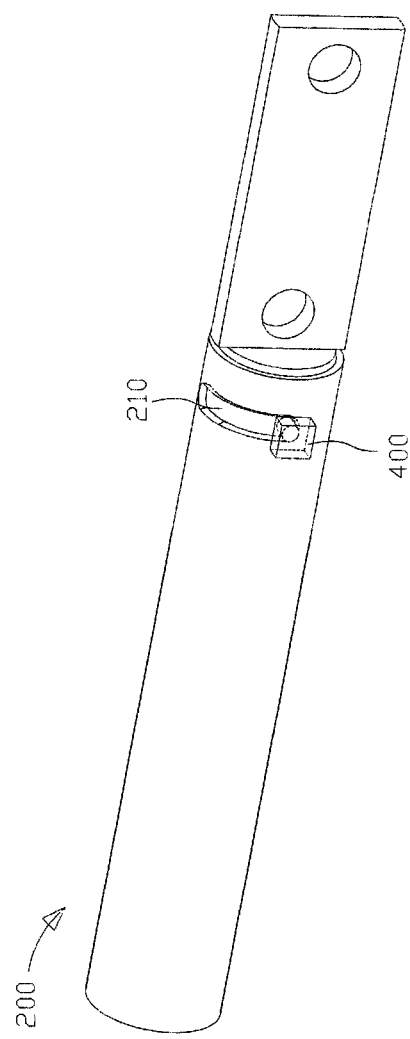
FIG. 11 is a schematic drawing showing a rotation angle between a sensor and a rotation assembly of the embodiment in FIG. 10 according to the present invention.
Figure 12:
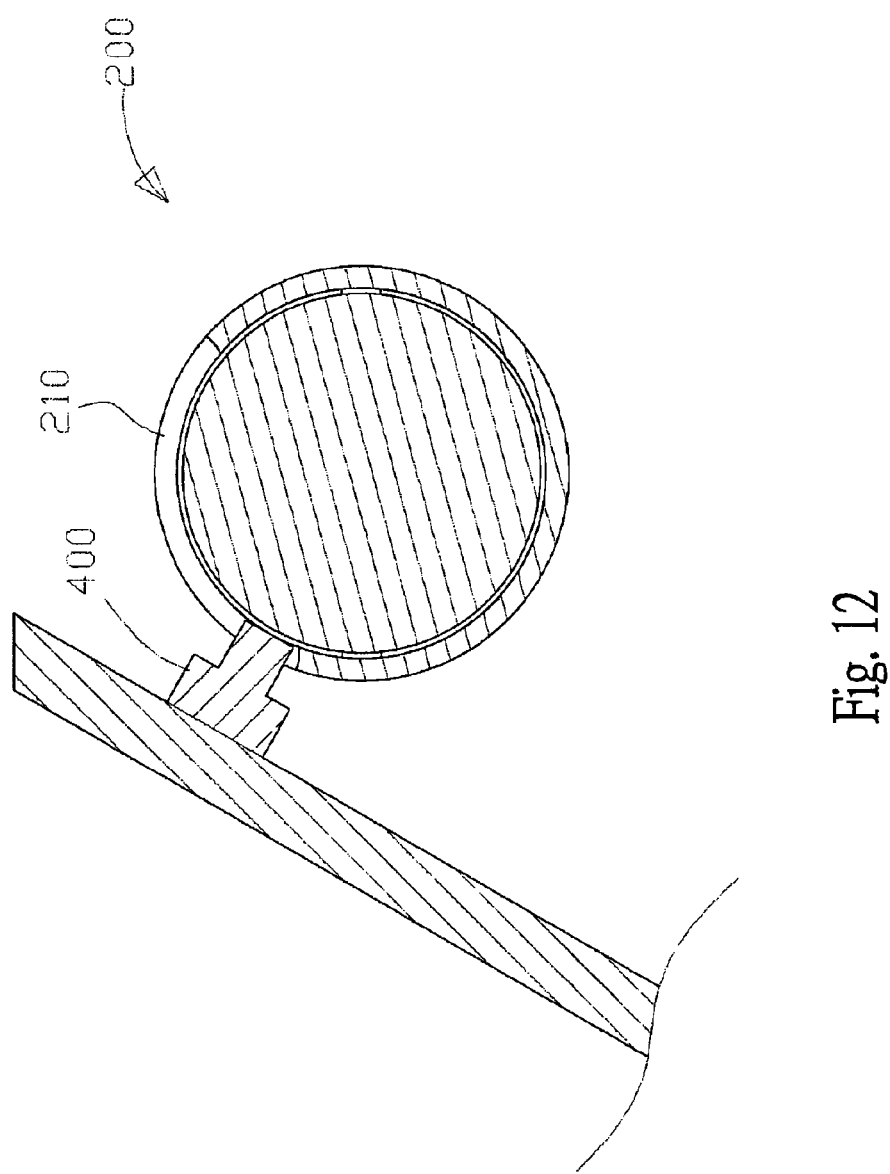
FIG. 12 is a cross sectional view of the embodiment in FIG. 10 showing a rotation angle between a sensor and a rotation assembly according to the present invention.

Refer to FIG. 10, FIG. 11, and FIG. 12, these are schematic drawings of an embodiment showing an image on the display 300 and a rotation angle between the sensor 400 and the rotation assembly 200. The sensor 400 of the present invention can be a contact sensor or a non-contact sensor. In this embodiment, the sensor 400 is a push button switch, a kind of contact sensor. As shown in FIG. 11, the sensor 400 is located at the lowest position of the limiting slot 210 of the hollow tube 220. Refer to FIG. 12, the sensor 400 is on the left side of the limiting slot 210. At the moment, the sensor 400 is leaning against the side wall of the rotating shaft 230 and an image of forward "A" is shown on the display 300 (as shown in FIG. 10).

Figure 13:
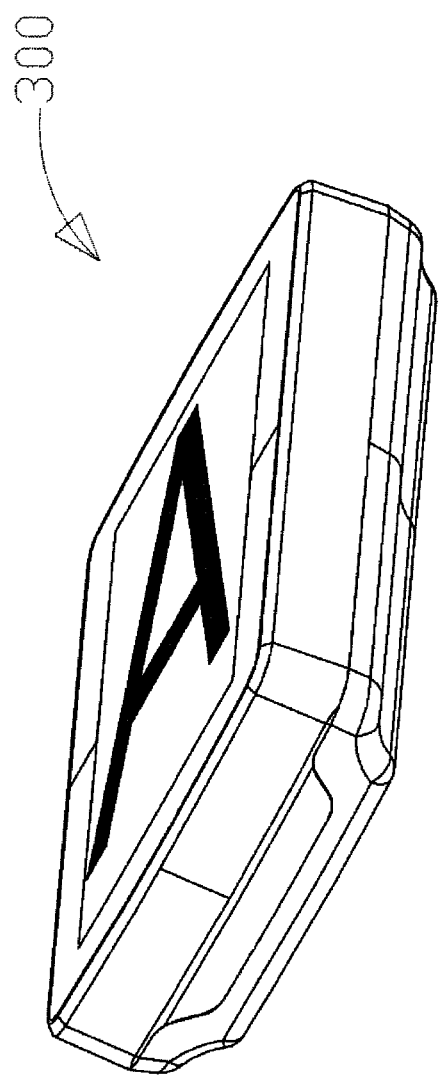
FIG. 13 is a schematic drawing showing an image on a display of another embodiment according to the present invention.
Figure 14:
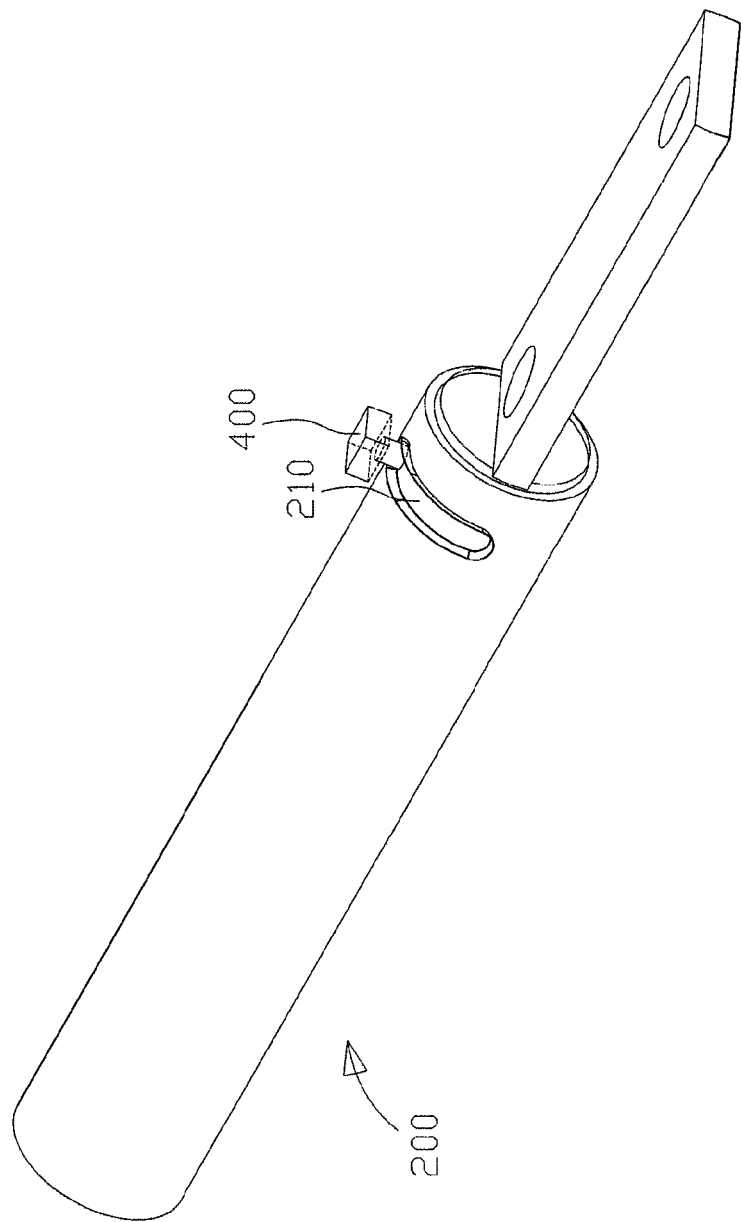
FIG. 14 is a schematic drawing showing a rotation angle between a sensor and a rotation assembly of the embodiment in FIG. 13 according to the present invention.
Figure 15:
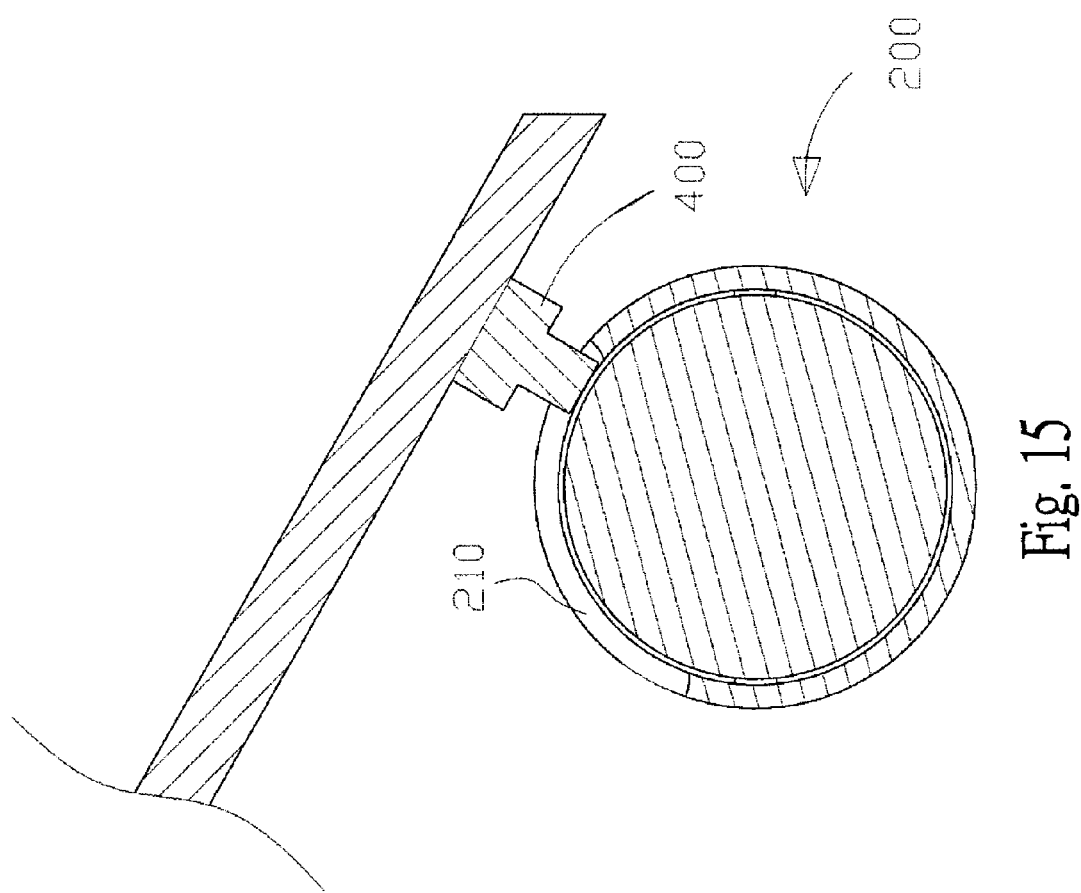
FIG. 15 is a cross sectional view of the embodiment in FIG. 13 showing a rotation angle between a sensor and a rotation assembly according to the present invention.

Refer to FIG. 13, FIG. 14, and FIG. 15, these are schematic drawings of another embodiment showing an image on the display 300 and a rotation angle between the sensor 400 and the rotation assembly 200. The difference between this embodiment and the above embodiment is in that the display 300 of this embodiment is rotated about 90 degrees clockwise. Now the sensor 400 is still located in the limiting slot 210 and the sensor 400 is moved to the highest position of the limiting slot 210 (as shown in FIG. 14). Refer to FIG. 15, the sensor 400 is on the right side of the limiting slot 210 and the sensor 400 is still leaning against the side wall of the rotating shaft 230. Viewed at the same angle, the image shown on the display 300 is still the image of forward "A", as shown in FIG. 13.

Figure 16:
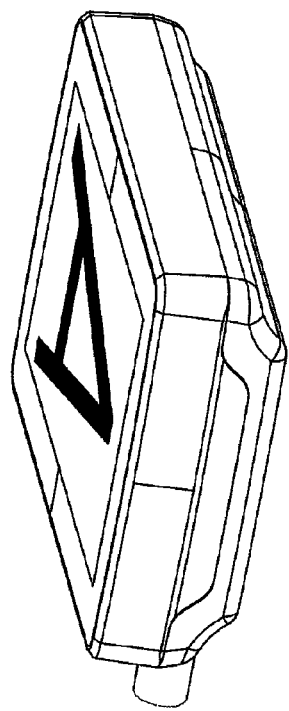
FIG. 16 is a schematic drawing showing an image shown on a display of a further embodiment according to the present invention.
Figure 17:
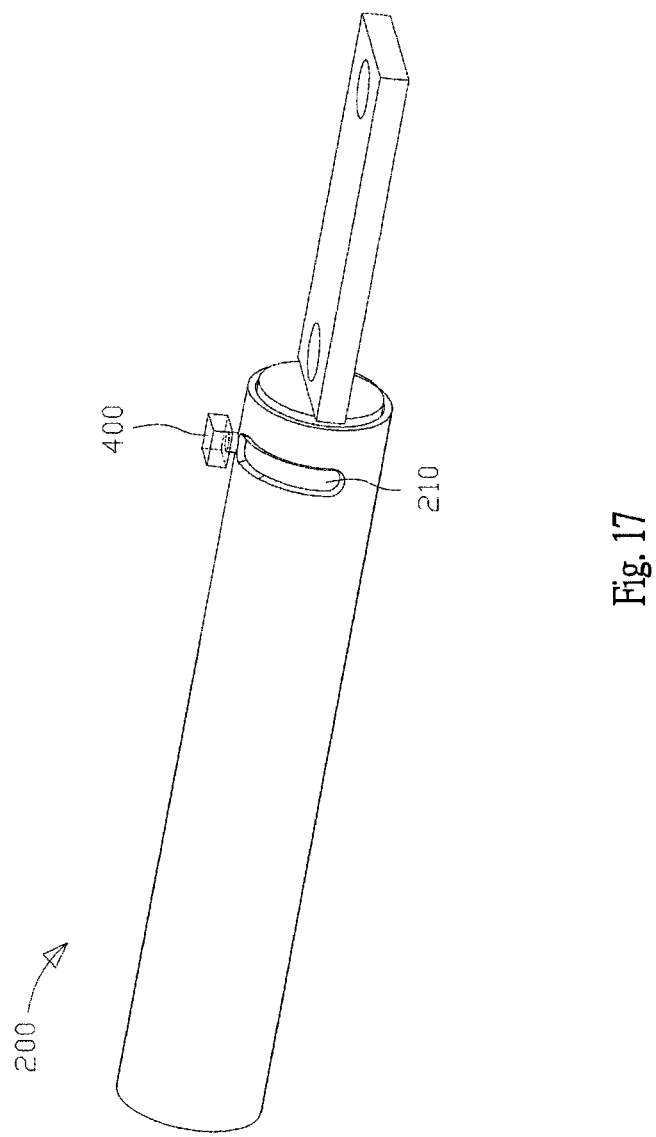
FIG. 17 is a schematic drawing showing a rotation angle between a sensor and a rotation assembly of the embodiment in FIG. 16 according to the present invention.
Figure 18:
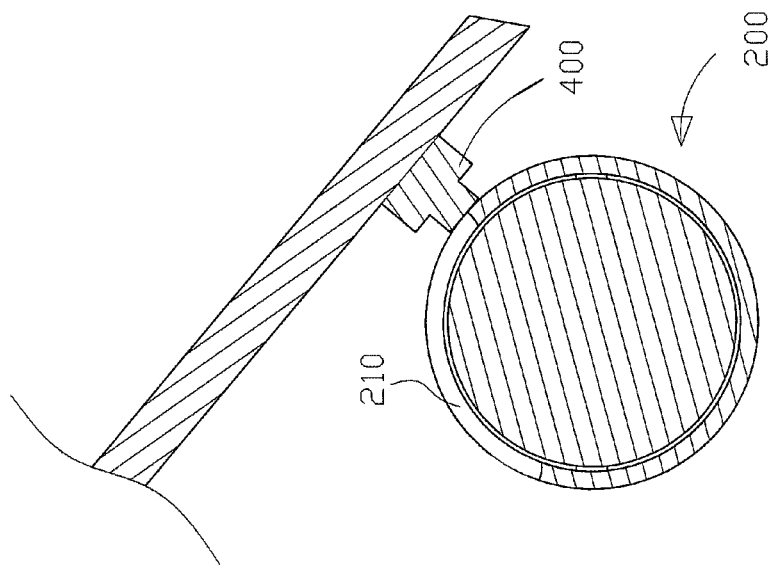
FIG. 18 is a cross sectional view of the embodiment in FIG. 16 showing a rotation angle between a sensor and a rotation assembly according to the present invention.

Refer to FIG. 16, FIG. 17, and FIG. 18, these are schematic drawings of another embodiment showing an image on the display 300 and a rotation angle between the sensor 400 and the rotation assembly 200. The difference between this embodiment and the above embodiment is in that the display 300 of this embodiment is continuingly rotated clockwise so as to make the sensor 400 slide out of the upper edge of the limiting slot 210 and lean against the side wall of the hollow tube 220. In this embodiment, the sensor 400 is a push button switch. The sensor 400 is triggered by a height difference between the limiting slot 210 and the hollow tube 220 while the sensor 400 is slid out of the limiting slot 210 clockwise. Thus a detection signal is generated and transmitted to the display 300 by the sensor 400 for driving the display 300 to reflect the image. Compared the embodiment in FIG. 16 and the above one in FIG. 13, an image of reverse "A" is shown on the display 300 of this embodiment. Thereby whether the display 300 reflects the image is determined according to whether the sensor 400 is in the limiting slot 210 or not in the present invention. Thus the image can be adjusted automatically and the present invention is more convenient for the user to use.

On the other hand, when the display 300 is rotated counterclockwise to allow the sensor 400 being slid from the side wall of the hollow tube 220 back to the limiting slot 210, the sensor 400 stops generating the detection signal. Thus the display 300 stops reflecting the image and the image displayed is changed from the reverse "A" back to the forward "A".

Figure 19:
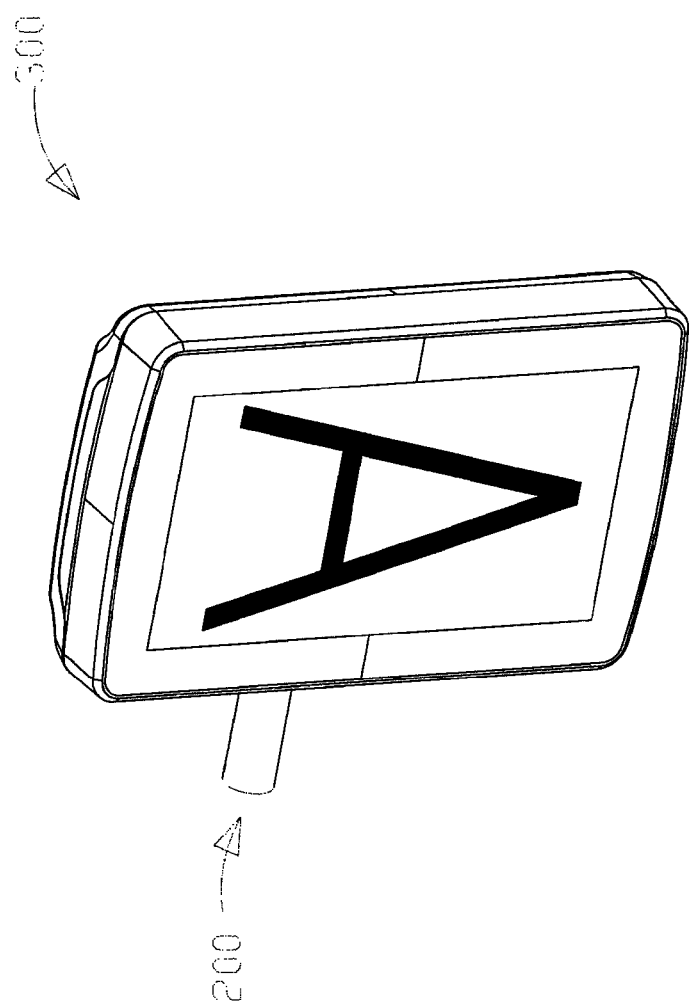
FIG. 19 is a schematic drawing showing an image shown on a display of a further embodiment according to the present invention.
Figure 20:
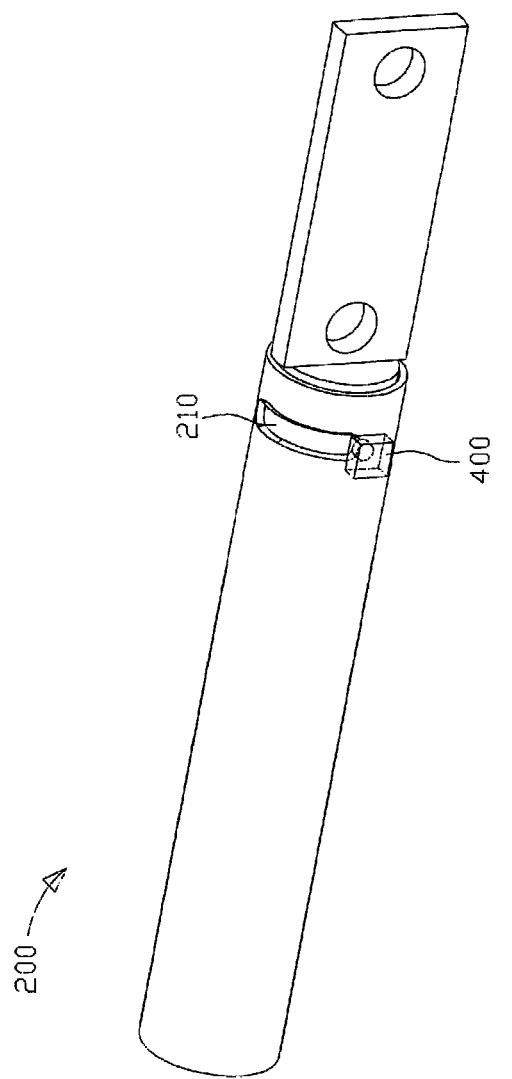
FIG. 20 is a schematic drawing showing a rotation angle between a sensor and a rotation assembly of the embodiment in FIG. 19 according to the present invention.
Figure 21:
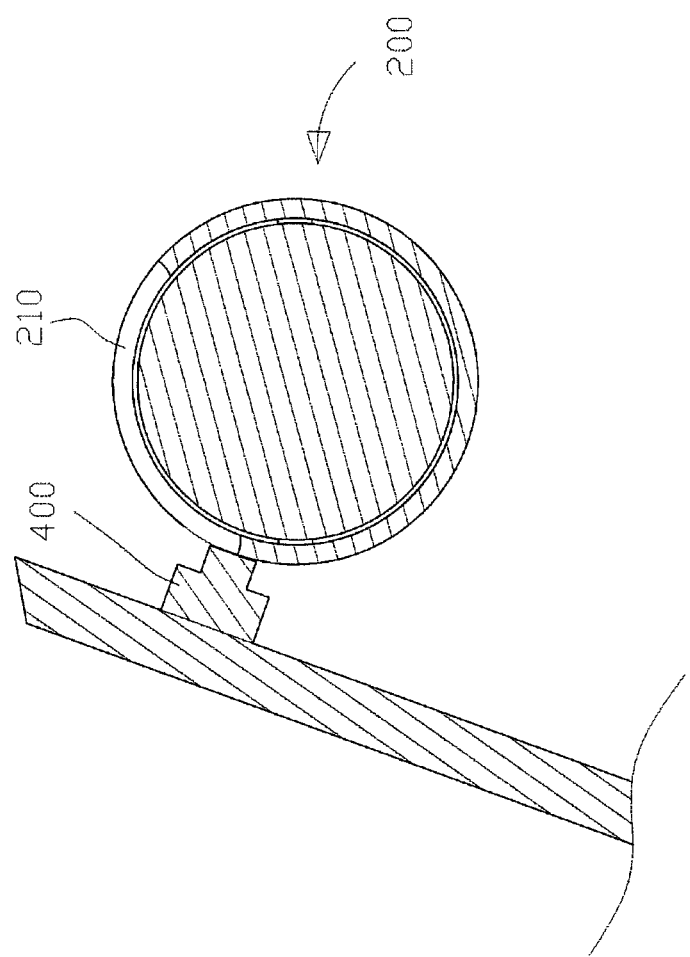
FIG. 21 is a cross sectional view of the embodiment in FIG. 19 showing a rotation angle between a sensor and a rotation assembly according to the present invention.

Refer to FIG. 19, FIG. 20, and FIG. 21, these are schematic drawings of another embodiment showing an image displayed on the display 300 and a rotation angle between the sensor 400 and the rotation assembly 200. The difference between this embodiment and the first embodiment in FIG. 10 is in that the display 300 of this embodiment is rotated counterclockwise to make the sensor 400 slide out of the lowest edge of the limiting slot 210 and lean against the side wall of the hollow tube 220. The sensor 400 in this embodiment is a push button switch. The sensor 400 is triggered by a height difference between the limiting slot 210 and the hollow tube 220 while the sensor 400 is slid out of the limiting slot 210 counterclockwise. Thus a detection signal is generated and transmitted to the display 300 by the sensor 400 for driving the display 300 to reflect the image. Compared this embodiment in FIG. 19 and the first embodiment in FIG. 10, an image of reverse "A" is shown on the display 300 of this embodiment. Thereby whether the display 300 reflects the image is determined according to whether the sensor 400 is in the limiting slot 210 or not in the present invention. Thus the image can be adjusted automatically and the present invention is more convenient for the user to use.

Figure 22:
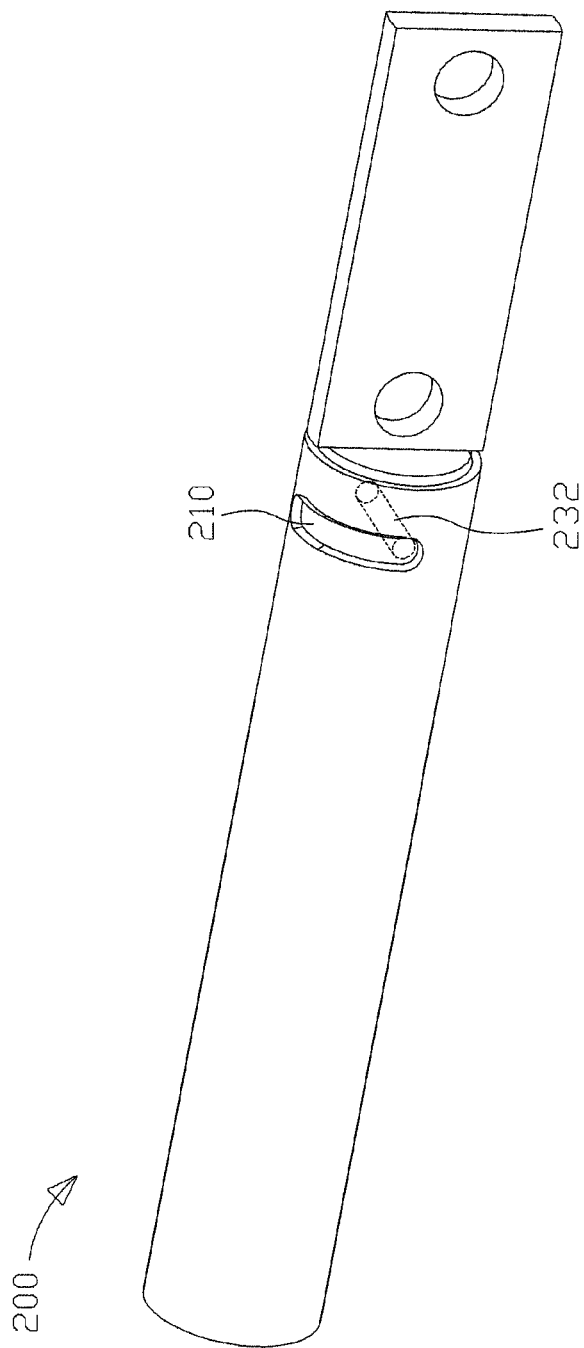
FIG. 22 is a perspective view of a rotation assembly of another embodiment according to the present invention.
Figure 23:
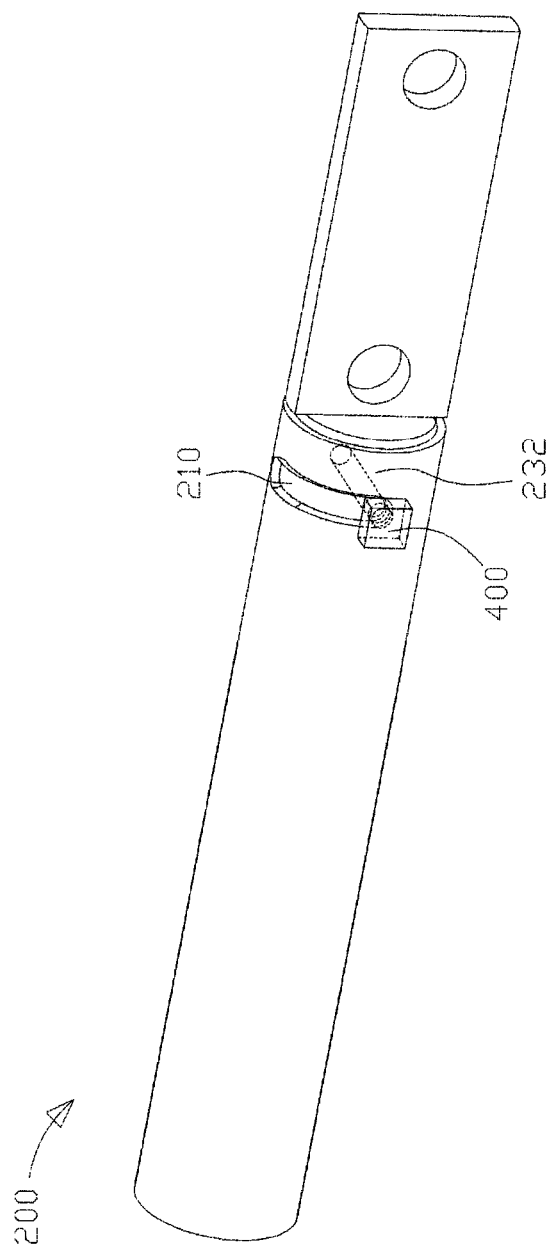
FIG. 23 is a perspective view showing a relative position of a sensor to a rotation assembly of the embodiment in FIG. 22 in use according to the present invention.
Figure 24:
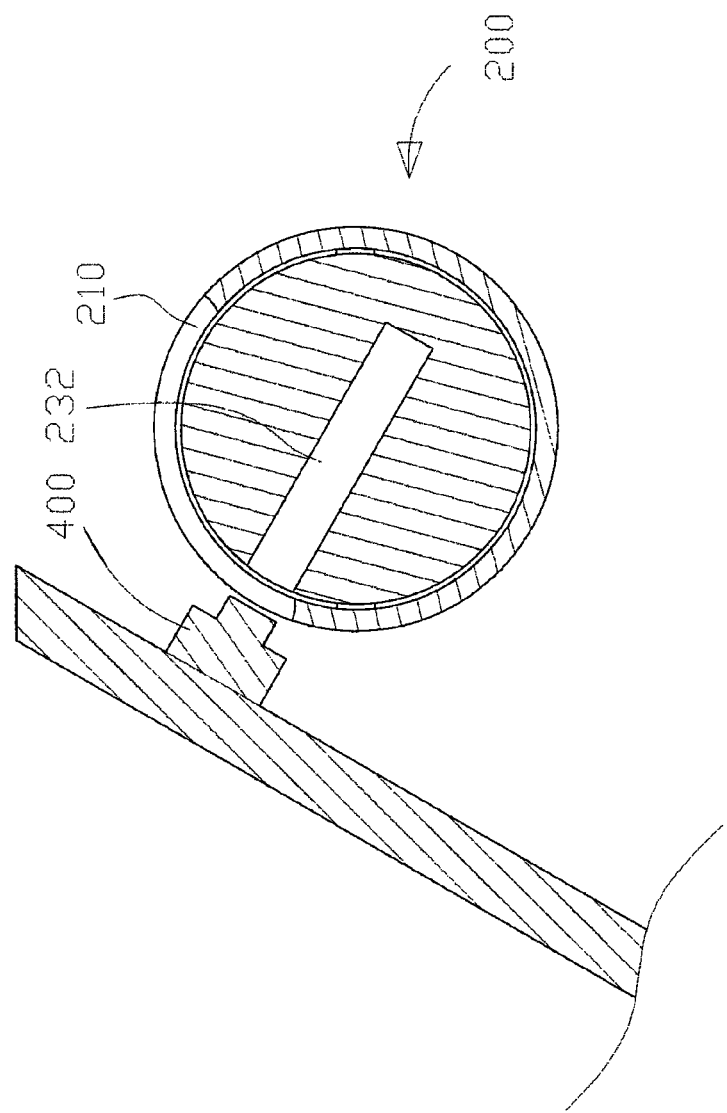
FIG. 24 is a cross sectional view showing a relative position of a sensor to a rotation assembly of the embodiment in FIG. 22 in use according to the present invention.

Refer to FIG. 22, FIG. 23, and FIG. 24, a perspective view of a rotation assembly of another embodiment according to the present invention, a perspective view and a cross sectional view of the embodiment in FIG. 22 showing the relative position of a sensor to a rotation assembly are revealed. The difference of this embodiment and the embodiment in FIG. 3 is in that the sensor 400 of this embodiment is a non-contact sensor. In this embodiment, the sensor 400 is a photo interrupter. The rotating shaft 230 of this embodiment is disposed with an insertion hole 232 whose position is corresponding to the sensor 400 (as shown in FIG. 23 and FIG. 24). When the sensor 400 is slid in the limiting slot 210, the insertion hole 232 is also slid correspondingly on the bottom of the limiting slot 210.

Figure 27:
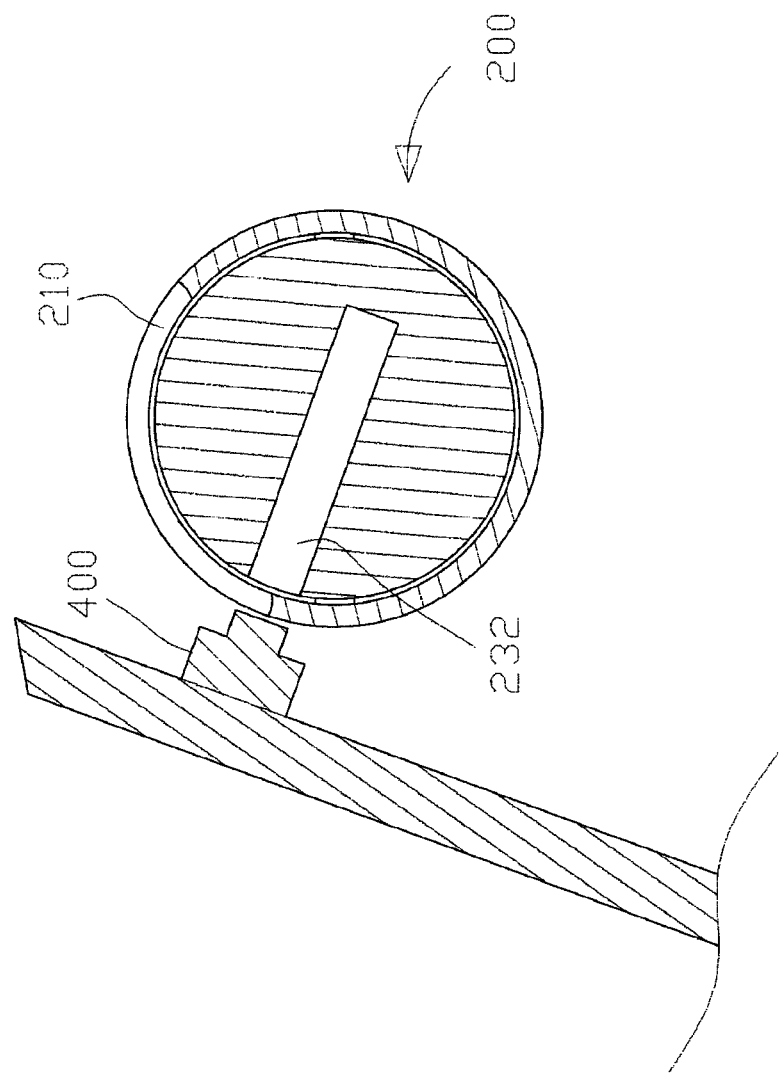
FIG. 27 is a further cross sectional view showing a relative position of a sensor to a rotation assembly of the embodiment in FIG. 22 in use according to the present invention.

In this embodiment, the sensor 400 is a photo interrupter that generates detection light and senses the detection light at the same time. A detection signal is generated if there is not detection light being sensed. Once the detection light is sensed, the detection signal is stopped generating. As shown in FIG. 27, the photo interrupter is slid inside the limiting slot 210 and the photo interrupter located at the leftmost of the limiting slot 210. The insertion hole 232 is corresponding to the photo interrupter so that the detection light generated from the photo interrupter can enter the insertion hole 232. Thus the photo interrupter will not generate and send the detection signal to the display 300. Therefore the display 300 will not reflect the image.

Figure 25:
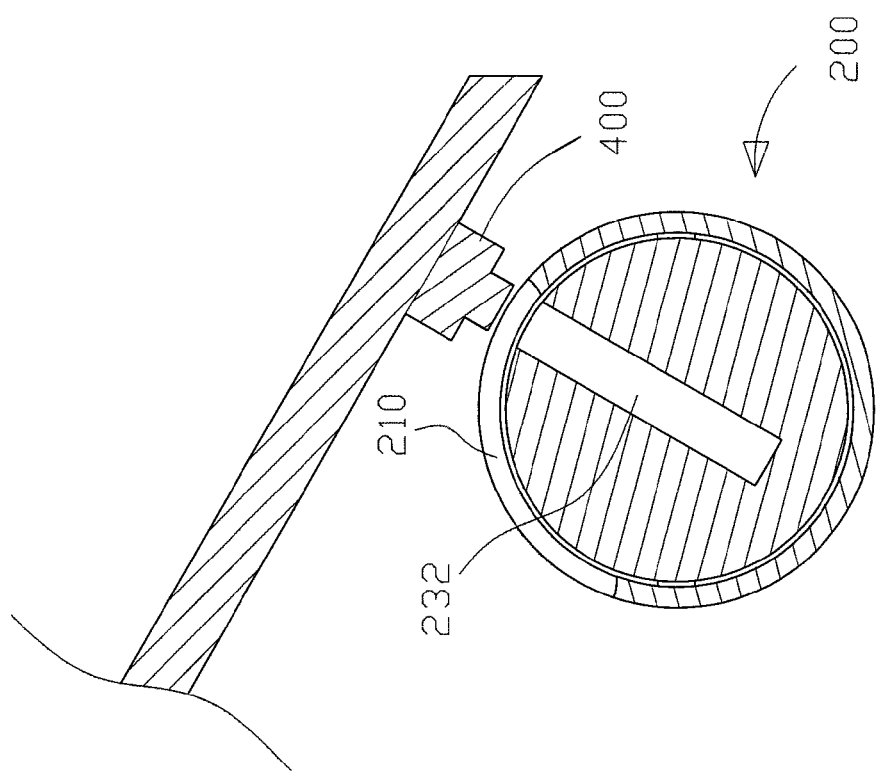
FIG. 25 is another cross sectional view showing a relative position of a sensor to a rotation assembly of the embodiment in FIG. 22 in use according to the present invention.

Refer to FIG. 25, the display 300 is rotated clockwise so that the sensor 400 (photo interrupter) is located at the rightmost of the limiting slot 210. Now the insertion hole 232 is still corresponding to the photo interrupter. Thus the detection light generated by the photo interrupter is projected into the insertion hole 232. Therefore no detection signal is generated by the photo interrupter and transmitted to the display 300 and the image is not reflected by the display 300.

Figure 26:
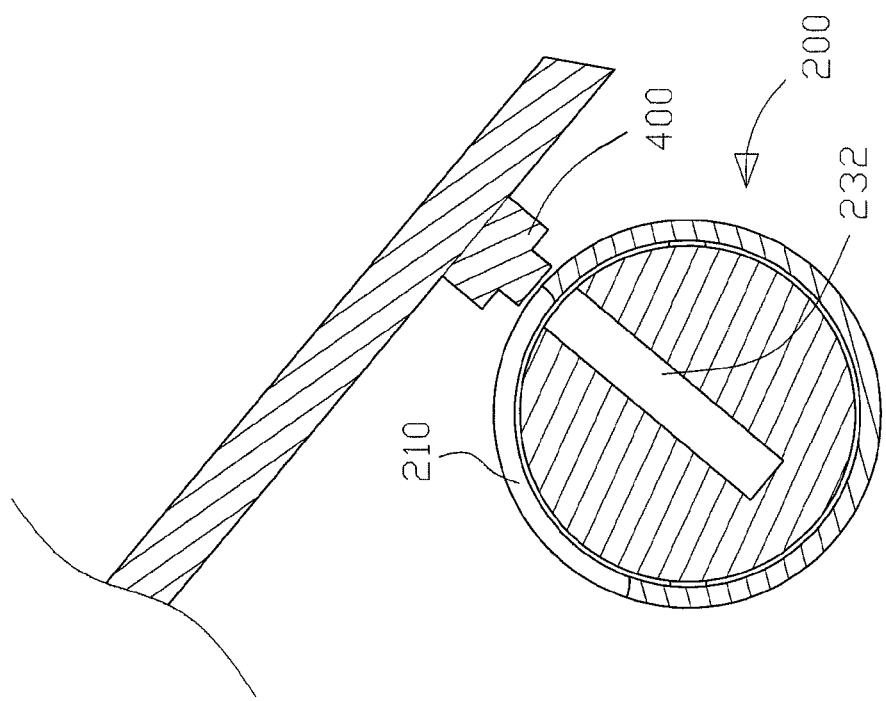
FIG. 26 is a further cross sectional view showing a relative position of a sensor to a rotation assembly of the embodiment in FIG. 22 in use according to the present invention.

Refer to FIG. 26, the display 300 is continuingly rotated clockwise so that the sensor 400 (photo interrupter) is slid to the surface of the hollow tube 220. Now the hollow tube 220 is located between the photo interrupter and the insertion hole 232. Thus the detection light transmitted from the photo interrupter to the insertion hole 232 is blocked. Then the photo interrupter senses no detection light and the photo interrupter generates the detection signal. The detection signal is transmitted to the display 300 for driving the display 300 to reflect the image captured now.

Refer to FIG. 27, the display 300 is continuingly rotated counterclockwise so that the sensor 400 (photo interrupter) is slid to the surface of the hollow tube 220. At the moment, the hollow tube 220 is located between the photo interrupter and the insertion hole 232 so that the detection light transmitted from the photo interrupter to the insertion hole 232 is blocked. Thus the photo interrupter senses no detection light and the photo interrupter generates the detection signal. The detection signal is transmitted to the display 300 for driving the display 300 to reflect the image.

Furthermore, in the present invention, the non-contact sensor can also be a capacitive sensor. Whether the sensor 400 is slid out of the limiting slot 210 is checked by the difference in capacitance between the conditions the sensor 400 is inside/outside the limiting slot 210. Thus whether the image captured is reflected or not by the display 300 is further controlled. People skilled in the art can easily appreciate the relationship of the gap distance between the sensor 400 and the limiting slot 210 to the capacitance value.

Figure 28:
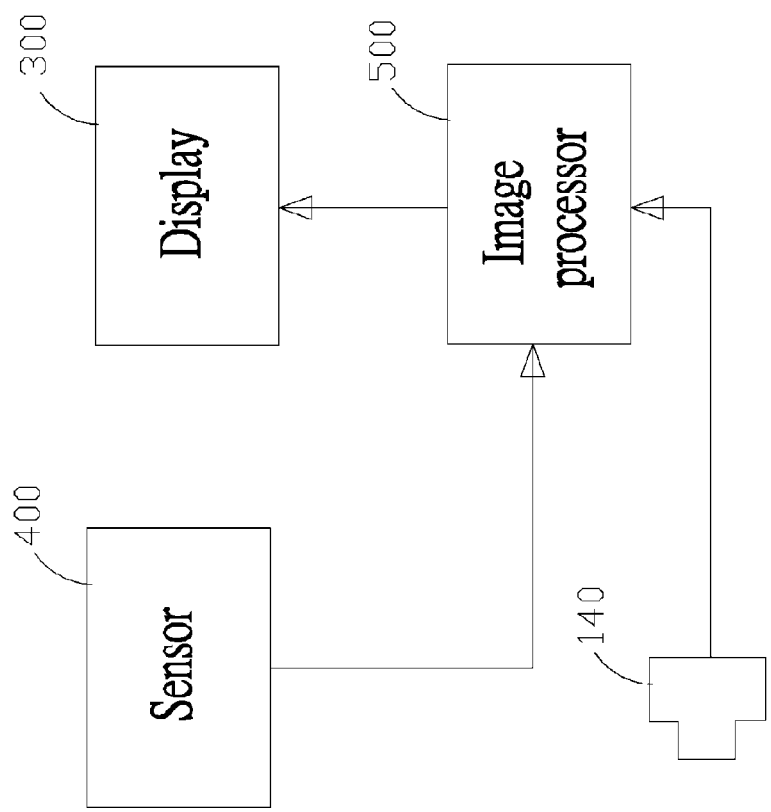
FIG. 28 is a circuit diagram of an embodiment according to the present invention.

Refer to FIG. 28, a circuit diagram of an embodiment of a laryngoscope of the present invention is revealed. As shown in the figure, the laryngoscope further includes an image processor 500 that is located in the display 300. The image processor 500 is used to receive the images captured by the camera lens 140 and the image processor 500 generate a plurality of image data. Then the image data is processed and transmitted to the display 300 by the image processor 500 so as to show the images on the display 300. The sensor 400 is used to detect the rotation angle of the display 300 for generating the detection signal and the sensor 400 transmitting the detection signal to the image processor 500. The image processor 500 reflects the plurality of image data according to the detection signal so that the display 300 shows the reflected image.

Whether the display 300 of the present invention reflects the image is determined according to whether the sensor 400 is inside the limiting slot 210 or not. The display 300 is rotated within a certain angle range. Once the display is rotated out of the range, the sensor 400 is driven to generate the detection signal so as to make the display 300 reflect the image.

In summary, a laryngoscope with automatic image adjustment of the present invention includes a laryngoscope body, a rotation assembly, a display and a sensor. The laryngoscope body is disposed with a fixing slot, the laryngoscope body is used for capturing an image. One end of the rotation assembly is fixed in the fixing slot while the other end thereof is arranged with the display. The rotation assembly is set with a limiting slot. The display is rotated around the rotation assembly. The sensor is electrically connected to a rear side of the display and the sensor is located inside the limiting slot. While the display being rotated, the sensor is slid on the surface of the rotation assembly. When the sensor is slid in the limiting slot, the display shows the image. Once the sensor is slid outside the limiting slot, the display shows a reflection of the image. Thus the image is adjusted automatically and the laryngoscope is more convenient for the user to use.

Thus the present invention is new, involving an inventive step and capable of industrial applications.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A laryngoscope with automatic image adjustment comprising:
   a laryngoscope body having a fixing slot;
   a rotation assembly having one end connected to the fixing slot, the rotation assembly arranged with a limiting slot;
   at least one display that is disposed on the other end of the rotation assembly; and
   at least one sensor that is electrically connected to a rear side of the display, the sensor is located inside the limiting slot; while the display being rotated, the sensor is slid on a surface of the rotation assembly; the display shows the image when the sensor is slid in the limiting slot while the display shows a reflection of the image once the sensor is not in the limiting slot;
   wherein the rotation assembly includes:
   a hollow tube that is fixed in the fixing slot, the hollow tube having the limiting slot disposed thereof; and
   a rotating shaft that is pivotally arranged in the hollow tube; the display is fixed and arranged at the rotation shaft; the sensor is leaning against a side wall of the rotating shaft while being slid in the limiting slot;
   wherein the laryngoscope body includes:
   a handle having a first end thereof arranged with the fixing slot;
   a tube that is disposed on a second end of the handle; and
   a camera lens that is mounted in the tube and located at a front end of the tube for capturing the image.

2. The device as claimed in claim 1, wherein the rotating shaft is further disposed with a fixing portion and the display is fixed on the fixing portion.

3. The device as claimed in claim 2, wherein the laryngoscope further includes a plurality of fasteners; a plurality of spacing holes is disposed on the fixing portion while a plurality of fixing holes is arranged at the display; positions of the fixing holes are corresponding to positions of the spacing holes; each of the fasteners is inserted through the spacing holes and then is fastened and fixed in the fixing holes respectively.

4. The device as claimed in claim 1, wherein the sensor is a contact sensor; the contact sensor is a push button switch.

5. A laryngoscope with automatic image adjustment comprising:
    a laryngoscope body having a fixing slot;
    a rotation assembly having one end connected to the fixing slot, the rotation assembly arranged with a limiting slot;
    at least one display that is disposed on the other end of the rotation assembly; and
    at least one sensor that is electrically connected to a rear side of the display, the sensor is located inside the limiting slot; while the display being rotated, the sensor is slid on a surface of the rotation assembly; the display shows the image when the sensor is slid in the limiting slot while the display shows a reflection of the image once the sensor is not in the limiting slot;
    wherein the rotation assembly includes:
    a hollow tube that is mounted in the fixing slot while the limiting slot is arranged at the hollow tube; and
    a rotating shaft that is pivotally arranged in the hollow tube; the display is fixed on the rotating shaft; the rotating shaft is disposed with an insertion hole and the position of the insertion hole is corresponding to the sensor; the insertion hole is slid correspondingly on the bottom of the limiting slot when the sensor is slid in the limiting slot;
    wherein the laryngoscope body includes:
    a handle having a first end thereof arranged with the fixing slot;
    a tube that is disposed on a second end of the handle; and
    a camera lens that is mounted in the tube and located at a front end of the tube for capturing the image.

6. The device as claimed in claim 5, wherein the rotating shaft is further disposed with a fixing portion and the display is fixed on the fixing portion.

7. The device as claimed in claim 6, wherein wherein the laryngoscope further includes a plurality of fasteners; a plurality of spacing holes is disposed on the fixing portion while a plurality of fixing holes is arranged at the display; positions of the fixing holes are corresponding to positions of the spacing holes; each of the fasteners is inserted through the spacing holes and then is fastened and fixed in the fixing holes respectively.

8. The device as claimed in claim 5, wherein the sensor is a non-contact sensor; the non-contact sensor is a photo interrupter.

9. The device as claimed in claim 5, wherein the laryngoscope body further includes:
    a blade that is disposed around the tube and connected to the second end of the handle; the blade having a transparent window for allowing the camera lens to take the image.

10. The device as claimed in claim 9, wherein the laryngoscope body further includes at least one lighting unit arranged at the camera lens and used for providing light to the camera lens.

\* \* \* \* \*